United States Patent [19]

Wilson et al.

[11] Patent Number: 5,639,798
[45] Date of Patent: Jun. 17, 1997

[54] PROCESS AND CATALYST FOR PRODUCTION OF HYDROCARBONS

[75] Inventors: Geoffrey Robert Wilson, Pittsburgh; Norman L. Carr, Wexford, both of Pa.

[73] Assignee: Wexford P.A. Syncrude Limited Partnership, Pittsburgh, Pa.

[21] Appl. No.: 485,351

[22] Filed: Jun. 7, 1995

Related U.S. Application Data

[63] Continuation-in-part of Ser. No. 356,697, Dec. 15, 1994.

[51] Int. Cl.$^6$ .................... B01J 23/00; C07C 27/00
[52] U.S. Cl. .................. 518/714; 518/715; 502/308; 502/321
[58] Field of Search .................... 502/308, 314, 502/321, 322; 518/714, 715

[56] References Cited

U.S. PATENT DOCUMENTS

| | | | |
|---|---|---|---|
| 3,752,774 | 8/1973 | Stiles | 252/462 |
| 4,177,202 | 12/1979 | Chang et al. | 260/449 R |
| 4,385,193 | 5/1983 | Bijwaard et al. | 585/310 |
| 4,499,209 | 2/1985 | Hoek et al. | 518/707 |
| 4,522,939 | 6/1985 | Minderhoud et al. | 502/242 |
| 4,523,047 | 6/1985 | Chester et al. | 585/322 |
| 4,558,030 | 12/1985 | Arcuri et al. | 502/325 |
| 4,587,008 | 5/1986 | Minderhoud et al. | 208/109 |
| 4,605,751 | 8/1986 | Curtis et al. | 556/29 |
| 4,613,624 | 9/1986 | Beuther et al. | 518/715 |
| 4,657,885 | 4/1987 | Fiato et al. | 502/241 |
| 4,686,238 | 8/1987 | Bode et al. | 518/700 |
| 4,774,261 | 9/1988 | Przydrozny et al. | 518/714 |
| 4,801,573 | 1/1989 | Eri et al. | 502/302 |
| 4,880,763 | 11/1989 | Eri et al. | 502/302 |
| 5,102,851 | 4/1992 | Eri et al. | 502/302 |
| 5,116,879 | 5/1992 | Eri et al. | 518/716 |
| 5,138,111 | 8/1992 | Kugler et al. | 585/277 |
| 5,140,050 | 8/1992 | Mauldin et al. | 518/715 |
| 5,162,284 | 11/1992 | Soled et al. | 502/324 |
| 5,302,622 | 4/1994 | Chaumette et al. | 518/713 |

*Primary Examiner*—C. Warren Ivy
*Assistant Examiner*—Karl J. Puttlitz, Jr.
*Attorney, Agent, or Firm*—Douglas Baldwin

[57] ABSTRACT

A catalyst and slurry reactor Fischer-Tropsch conversion process utilizing novel catalysts comprising cobalt promoted with molybdenum or molybdenum and zirconium on a small diameter inorganic oxide support. The catalysts have been found to be highly selective for production of liquid hydrocarbons while minimizing production of less desirable oxygen-containing products such as alcohols. The preferred catalysts contain from about 5% to 50% cobalt and from about 0.1% to 10% molybdenum or molybdenum and zirconium.

10 Claims, No Drawings

PROCESS AND CATALYST FOR PRODUCTION OF HYDROCARBONS

This application is a continuation-in-part of U.S. patent application Ser. No. 08/356,697 filed Dec. 15, 1994, which is currently pending.

BACKGROUND OF THE INVENTION

This invention relates to catalysts having improved activity for the production of hydrocarbons from hydrogen and carbon monoxide and to an improved hydrocarbon synthesis process. Specifically, this invention relates to a catalyst comprising cobalt supported on an inorganic oxide promoted by molybdenum and or molybdenum and zirconium.

The conversion of mixtures of carbon monoxide and hydrogen, for example synthesis gas or syngas, is commonly referred to as Fischer-Tropsch synthesis. Fischer-Tropsch synthesis was used extensively in Germany during World War II. There is considerable incentive for use of the process in the conversion of coal to liquid fuels and for conversion of natural gas to liquid fuels. Liquid fuels are more easily transported and utilized than coal. Conversion of natural gas to liquid makes transportation and storage more feasible. Sasol operates commercial Fischer-Tropsch plants in South Africa which employ an iron catalyst (see for example *Oil and Gas Journal*, Jan. 20, 1992, p. 53). A large commercial plant using Shell Oil technology has been recently placed in production in Malaysia. These commercial operations typically employ fixed-bed reactor systems.

Slurry phase reactors, especially slurry bubble column reactor systems (SBCR), for Fischer-Tropsch processes have received considerable attention in recent years. The slurry process has a number of advantages, including the ability of the reactor to handle the large heats of reaction and thereby control reaction temperature; the ability to convert low $H_2/CO$ ratio synthesis gas without the need for a separate water-gas shift process step; and relatively low capital and operating costs. (See *Hydrocarbon Processing*, "Catalysts for Fischer-Tropsch," February 1990 pp. 59–68.) Slurry reactor systems are characterized by suspending the Fisher-Tropsch catalyst in an upflow of synthesis gas in a liquid medium. Basically, the process includes a finely divided catalyst suspended in oil that is mixed in a reactor (e.g. a SBCR) in the presence of synthesis gas. Early patents describing the slurry process are U.S. Pat. Nos. 2,438,029; 2,680,126; 2,852,350 and others. Slurry reactor systems are discussed in the article "Fisher-Tropsch Synthesis in the Slurry Phase," M. D. Schlesinger et al., *Industrial Engineering Chemistry*, Vol. 6, p. 1474 (1951). U.S. Pat. No. 4,252,736 discloses a process in which syngas is continuously bubbled through a column of Fisher-Tropsch catalyst suspended in oil.

In principle, all catalysts that are active for Fisher-Tropsch synthesis can be used in slurry reactor systems. The objective of catalyst choice is to obtain the highest possible selectivity of desired liquid hydrocarbon products and the highest possible activity. Iron catalysts have been preferred because of low cost and good activity. However, better catalyst-reactor systems are desired. U.S. Pat. No. 5,162,284 to Soled et al. describes a copper promoted cobalt manganese spinel catalyst.

Common Fischer-Tropsch catalysts are cobalt, and iron (see for example, "The Fischer-Tropsch Synthesis," by R. B. Anderson, *Academic Press* (1984), p. 2). Other Group VIII metals such as ruthenium and osmium are also active. Other metals that have been investigated as primary catalyst components include rhenium, molybdenum, and chromium, but these have very low or no activity and produce primarily methane.

The activity of supported cobalt catalysts can be enhanced, or the performance modified, by the addition of a variety of metals. Exemplary metals include copper (U.S. Pat. Nos. 5,302,622 and 5,162,284), cerium (U.S. Pat. Nos. 3,888,792; 4,657,885; 4,801,573 and 4,880,763), rhenium (U.S. Pat. Nos. 4,088,671; 4,558,030; 4,568,663; 4,801,573 and 4,880,763) and manganese (U.S. Pat. No. 5,162,284). Precious metals include platinum, iridium, ruthenium and rhodium (U.S. Pat. Nos. 5,302,622; 5,059,574 and 5,102,851). In addition to enhancing catalyst activity, promoters are added to achieve specific results, e.g., to enhance liquid hydrocarbon production, to suppress methane production, etc. See, for example, the discussion in U.S. Pat. No. 4,880,763. U.S. Pat. No. 5,302,622 to Chaumette, et al. references French Patent Application No. 91/07,634 that describes a catalyst containing cobalt, at least one additional element chosen from molybdenum and tungsten and at least one element chosen from elements including ruthenium and copper.

A series of Shell patents (U.S. Pat. Nos. 4,522,939; 4,499,209; 4,587,008 and 4,686,238) disclose supported cobalt-silica catalysts promoted with zirconium, titanium or chromium. These catalysts are designed for fixed bed operation. Their effectiveness is dependent on the specific nature of metal incorporation on the support, i.e., by sequential impregnations and/or kneading.

U.S. Pat. Nos. 4,801,573 and 4,880,763 recite the use of small amounts of promoter oxides chosen from elements in Groups IIIB, IVB and VB (including zirconia but no promotional effect on either activity or selectivity was shown).

In view of the known tendency of molybdenum containing catalysts to lower Fisher-Tropsch synthesis activity and to increase methane production or the use of molybdenum as a promoter only with additional promoters, it was surprising to discover that cobalt catalysts could be effectively promoted to excellent activity and improved liquid hydrocarbon selectivity by incorporation of molybdenum and/or molybdenum together with zirconium. This invention shows such an improved catalyst in a slurry phase reactor and catalyst.

SUMMARY OF THE INVENTION

It has been unexpectedly found that the addition of molybdenum or molybdenum together with zirconium on an inorganic oxide support, preferably alumina, substantially increases the effectiveness of cobalt catalysts useful for the conversion of synthesis gas to hydrocarbons.

A slurry reactor process utilizing these catalysts has been found to be highly selective for production of liquid hydrocarbons while minimizing production of less desirable oxygen-containing products such as alcohols. The preferred catalyst contain from about 5% to 50% cobalt and from about 0.1% to 10% molybdenum or molybdenum and zirconium. Specifically, the improved catalyst comprises molybdenum, cobalt and an alumina support, the catalyst containing from about 2% to 50% cobalt and from about 0.1% to 15% molybdenum and optionally from about 0.1% to 10% zirconium, based on the total weight of the catalyst, the weight ratio of molybdenum to cobalt being from about 0.02 to 0.25 and the support having a particle size range of about 5 to 250 microns.

Other advantages and features will be apparent from the following description and from the claims.

DESCRIPTION OF THE PREFERRED EMBODIMENTS

The catalysts of the present invention comprise cobalt supported on an inorganic oxide which is promoted with molybdenum. These catalysts have been found to have high activity for the conversion of synthesis gas with high selectivity to liquid hydrocarbons. The observed Schulz-Flory alpha values are high corresponding to high potential yields of middle distillates.

Cobalt is added to an inorganic oxide support in amounts up to 50 wt. % of the final catalyst. Preferably, amounts between 5 and 45 wt. %; more preferably amounts between 10 and 40 wt. %, and most preferably between 20 and 30 wt. % are employed. The amount of molybdenum is preferably between 0.1 and 10 wt. %, and more preferably between 2 and 7 wt. %.

The support has a high surface area to more effectively disperse the catalytic components. The surface area is preferably greater than about 50 m$^2$/g, and the pore volume is preferably greater than 0.4 ml/g. Alumina is particularly suitable for the support and may be in any of the crystallographic forms such as gamma, eta, xi, theta, delta, kappa or mixtures thereof. X-ray amorphous aluminas, such as those derived by high temperature activation of alumina trihydrates such as gibbsite, may also be used. Silica alumina is also suitable. For the preferred slurry process of this invention, the support is in the form of microspheres with a particle size range of 5 to 250 microns, more preferably of 5 to 100 microns, and most preferably of 10 to 75 microns. The microspheres can be made in any suitable manner known in the art, but are usually prepared by spray drying a liquid solution of suitable alumina compound through a spray nozzle sized to provide the desired spherical shaped dried microspheres.

CATALYST PREPARATION

The catalytic metals are incorporated on the support by any suitable method, but impregnation of the support with solutions of the catalytic metals is preferred. Impregnation is accomplished either by the incipient wetness method or by using an excess of impregnating solution followed by evaporation of the excess liquid. It is preferred that impregnation be made from aqueous solutions of water soluble salts of the metals, but organic solvents having low boiling points can also be used.

Water is the especially preferred solvent when the catalytic metal salt is highly soluble in water, such as Cobalt nitrate, acetate or chloride. Similarly, ammonium molybdate gives suitable aqueous solutions. The catalytic metals can be applied either separately or from a common solution. It is preferred that they be applied from a common solution, i.e., co-impregnated. When applied separately, the support is dried after impregnation at a temperature between 80° and 130° C. for several hours to remove the excess water. The catalyst is similarly dried after the final impregnation, usually for a period of at least 4 hours but typically overnight. The catalyst may be calcined in air or hydrogen prior to use. If calcination in air is first performed prior to reduction in hydrogen, temperatures are suitably 250° to 550° C. and preferably 300° to 350° C. for both calcination and reduction.

Before use, the catalyst is activated in flowing hydrogen fluidized bed. This is done in a reduction apparatus in which hydrogen is passed over the catalyst at an elevated temperature. The reduction is carried out at atmospheric pressure or at elevated pressure. Low pressure is preferred to minimize the effect of water on the catalyst. Typically, the temperature of the catalyst in the reduction unit is increased at a rate of between 0.5° and 2° C./min from ambient to a final level of between 250° and 450° C., preferably between 300° and 400° C., and more preferably between 325° and 375° C. and maintained at the maximum temperature for about 6 to 24 hours, more preferably 10 to 24 hours.

After reduction, the catalyst may be partially re-oxidized in a diluted oxygen-containing atmosphere to "passivate" or reduce its tendency to be pyrophoric. If passivated, the catalyst is re-reduced, at conditions similar to those described above, prior to use in the process. The reduced catalyst is suitably protected from re-oxidation prior to introduction into the slurry reactor.

A convenient protection method is to cover the catalyst with a high molecular weight hydrocarbon such as Chevron Synfluid or liquid product from the Fischer-Tropsch process.

PROCESS

A variety of reactor configurations, such as fixed bed, fluidized bed, or slurry type reactors well known to those skilled in the art, are suitable for the Fischer-Tropsch process. The process of this invention is a slurry system, and the catalysts of this invention are particularly suited for slurry phase process application, particularly a process using a slurry bubble column reactor (SBCR) system. The catalysts have a particle size range of 5 to 250 microns, more preferably in the range of 5 to 100 microns, and most preferably in the range of 10 to 75 microns. For fixed bed reactors the catalyst supports may be in the form of extrudates, spheres or granules, but it is highly preferred that they be microspheres, and preferably alumina microspheres, for use in the SBCR system.

The process is carried out in a slurry reactor, and preferably a bubble column slurry reactor. The slurry process offers a number of advantages including better control of the removal of exothermic heat produced in the Fisher-Tropsch synthesis and better control over catalyst activity maintenance by allowing continuous recycle, and continuous catalyst make-up and removal, recovery and rejuvenation.

The slurry reaction system comprises a suitable catalyst suspended in a liquid medium suitable for the purpose of converting syngas to hydrocarbons products. Basically, the slurry catalyst process constitutes a process in which the small diameter or finely divided catalyst having a particle size of about 5 to 75 microns is mixed in oil and is circulated by synthesis gas flow through a reactor. The bubble column reactor slurry process is a process in which syngas is continuously bubbled through a column of catalyst suspended in oil.

A carbon monoxide/hydrogen mixture is forced through the catalyst slurry in a manner and at a rate to allow intimate contact between the CO/H$_2$ and catalyst. The process is operated in either a batch or continuous liquid recycle. In the continuous process, only the liquid is circulated in the system. The slurry liquid used in the process is liquid at reaction temperatures and must be chemically inert under reaction conditions. It must also be a relatively good solvent for CO/H$_2$ and possess good slurrying and dispersion properties for the finely divided catalyst. Representative classes of organic liquids that can be used include high boiling paraffins and aromatic hydrocarbons. High boiling paraffins include $C_{10}$–$C_{50}$ linear or branched paraffin; the aromatic hydrocarbons include $C_6$–$C_{20}$ single ring and multiple ring aromatics.

The slurry liquid can contain N or O in the molecular structure but substantially no S, P, As or Sb, since these elements form poisons in the slurry process. Specific liquids are dodecane, tetradecane, hexadecane, octadecane, cosane, tetracosane, tetracosane, tetracosane, and the like. Octacosane and hexadecane are particularly suitable, as are certain commercially available liquid hydrocarbons such as Chevron Synfluid, a product available from Chevron Chemical Company.

The concentration of catalyst used in the liquid hydrocarbon slurry solvent is generally about 10 to 60 grams of dry catalyst per 500 grams of slurry liquid; preferably, about 30 to 50 grams dry catalyst per 500 grams slurry liquid, i.e., 25 to 150 grams per liter.

In a typical laboratory unit the slurry is preferably stirred to promote good dispersion to avoid catalyst settling and to reduce mass transfer limitations between gas and liquid. Stirring rate is generally in the range of about 600 to 1200 rpm for laboratory sized turbines.

The reactor is typically purged with $N_2$ (or other inert gas) prior to introduction of syngas to remove any reactive gases. It is heated to reaction temperature prior to introduction of the $CO/H_2$.

The $H_2/CO$ molar ratio is preferably in a molar ratio of 10:1 to 1:10, preferably 3:1 to 0.5:1, and especially 1:1 to 2:1. Temperatures are generally in the range of about 190° to 300° C., preferably about 220° to 240° C. Higher temperatures can be used but tend to produce lighter products. Lower temperatures tend to result in lower rates and increased wax formation. Useful reaction pressure is in the range of about 50 to 600 psig, and preferably about 70 to 400 psig. Space velocity is generally about 100 to 15000 volumes of gaseous feed per volume of dry catalyst in the slurry per hour, and preferably in the range of about 800 to 5000 v/v/hr. Higher space velocities lower CO conversion.

Carbon monoxide conversions are generally above 50%. Preferably, the reaction variables are adjusted to minimize carbon dioxide and methane production and to maximize carbon monoxide selectivity to $C_5$ to $C_{30}$ paraffins while achieving good catalyst activity maintenance.

Generally, a typical preferred mode of operation of a laboratory continuous stirred tank reactor (CSTR) includes using a highly paraffinic wax as the slurry liquid; a catalyst/ liquid ratio of about 100 grams per liter; stirring the reactor at 1,200 rpm; an $H_2/CO$ ratio of about 2:1; temperature of about 230° C.; pressure of about 175 psig and space velocity of about 2000 v/v/hr.

Effluent reactant gases from the process may be separated and recycled, if desired, for further hydrocarbon synthesis. Methods of collecting the products are well known and include fractional distillation and the like. The laboratory reactor is a continuous stirred tank reactor, and auxiliary equipment is conventional and known to those skilled in the art.

For laboratory testing, feed carbon monoxide syngas is purified and blended with hydrogen and or purge gas. The blend is metered into the reactor containing the catalyst slurry. Effluent vapor from the reactor is passed through a sequence of condensation traps: a first wax trap maintained at about 200° C.; a second wax trap maintained at about 100° C. and an oil trap maintained at about 0° C. The remaining gas is passed through a gas meter and to a chromatographic column for analysis or collected for analysis at a later time. Laboratory test conditions are summarized below:

| | |
|---|---|
| Temperature: C. | 190–300 |
| Synthesis Gas Pressure: bar | 5–40 |
| Space Time (*): g cat./Nl/hr | 0.1–5 |
| $H_2/CO$ mole ratio | 0.6–3 |

(*) Expressed as normal liters of carbon monoxide feed

TREATMENT OF RESULTS

In order to normalize catalyst activity data obtained at different reactor conditions in a continuously stirred tank reactor, kinetic equations are used to calculate relative activity as follows:

The kinetic model is $$K\theta = \frac{X(1+\alpha X)}{(1-X)} \text{ where}$$

K=a kinetic parameter with the units of reciprocal space time, which is proportional to hydrogen partial pressure in the feed gas to the power of 0.6 and to the relative activity (RA) of the catalyst θ=space time, expressed as grams of catalyst per normal liter of CO per hour X=fraction conversion of carbon monoxide in the reactor, expressed as $$\frac{(\text{feed CO} - \text{product CO})}{\text{feed CO}}$$

where the CO is expressed in moles per hour
α=the contraction factor for the reaction:

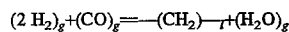

and is equal to −0.66.

Hydrocarbon selectivities are expressed on a carbon atom basis, as the percentage of converted CO which appears as a given product. For example:

$C_5+$ Selectivity: %=

$C_5$ + Selectivity: % =

$$\frac{(\text{Carbon Yield for all } C_5 + \text{hydrocarbons}) \times 100}{\text{Carbon converted to all hydrocarbons or } 100 - 100 \times (\text{sum fractional selectivities to } C_1, C_2, C_3 \text{ and } C_4)}$$

This selectivity term does not include the carbon converted to carbon dioxide.

The "Schulz-Flory alpha" is a known method for describing the product distribution in Fisher-Tropsch synthesis reactions. The Schulz-Flory alpha is the ratio of the rate of chain propagation to the rate of propagation plus termination and is described from the plot of ln(Wn/n) vs. n, where Wn is the weight fraction of products with a carbon number of n. The alpha value is thus indicative of the selectivity of the catalyst for producing heavy hydrocarbons from synthesis gas.

ILLUSTRATIVE EMBODIMENTS

CATALYST AND SUPPORT CHARACTERIZATION

Catalyst and support surface area and pore volume were determined by methods well known in the art. Surface area was measured by the BET method, while pore volume was determined either by the nitrogen adsorption method or by mercury intrusion.

CATALYST REDUCTION

Prior to determination of the Fischer-Tropsch synthesis gas conversion activity, a sample of each catalyst, in the form of microspheres of a typical size of between 38 and 106 microns, was pre-reduced in a fluid bed reduction apparatus. Hydrogen was passed into the reduction unit at a superficial velocity of 1 ft/sec (10.8 cu ft/hr) while heating the catalyst at a rate of 1° C./min to 350° C. This temperature was then maintained for 14 hours before cooling and discharging the catalyst under a nitrogen atmosphere. The reduced catalyst was weighed at this point. The reduced catalyst was mixed with about 300 g (about 400 ml) of Synfluid (Chevron Synfluid PAO 8) and added to the autoclave for measurement of its Fischer-Tropsch conversion activity.

HYDROCARBON SYNTHESIS PROCEDURE

A stirred autoclave reactor of 1 liter total volume was employed with continuous gas flow to determine the catalyst activity for Fischer-Tropsch conversion of synthesis gas at a system pressure in the range of 175 to 350 psig. An $H_2/CO$ molar ratio in the range of 1.7 to 2.2 was used at a total flow rate in the range of about 90 to 200 liters per hour. Catalyst charge weights were in the range of 30 to 50 grams in 500 ml reactor volume. Gas and liquid products were analyzed by chromatographic procedures. Product was collected for analysis to provide data for yields, conversions and material balance.

EXAMPLE 1

A solution of cobalt nitrate, $Co(NO_3)_2.6H_2O$, was dissolved in 49.2 ml distilled water. This solution was then added, with stirring, to 50.0 g of Vista Catapal alumina, which is a psuedoboehmite type alumina, which had been first calcined at 500° C. for 6 hours. An additional 63 ml of distilled water was added to provide excess liquid over the alumina. The excess liquid was then evaporated at 66° C. and the sample dried at 104° C. for 6.3 hours. The dried catalyst was then calcined in air at 500° C. for a period of 3.3 hours. The calcined catalyst was screened to provide a 38-75 micron fraction to the reduction unit. The final catalyst contained 16.7 wt. % cobalt. The Fischer-Tropsch conversion results are contained in Table 1.

EXAMPLE 2

A solution of cobalt nitrate was prepared by adding 49.39 g cobalt nitrate to 40.96 g water. This solution was added to 40.0 g of LaRoche Versal-GH alumina, which, according to the manufacturer, is derived from Versal-900 psuedoboehmite type alumina by calcination at 850° C. for a short period of time. The solution volume was in excess of the incipient wetness point. The excess liquid was evaporated on a hot plate and the catalyst transferred to an oven at 95° C. and dried overnight. The final catalyst was screened to a 38-106 micron fraction. The final cobalt content was 20.0 wt % on a water free basis. The Fischer-Tropsch conversion results are contained in Table 1.

EXAMPLE 3

A solution of cobalt nitrate containing 123.46 g of cobalt nitrate and 126 ml water was prepared and added to 100 g of LaRoche Versal-900 alumina which had been first calcined at 500° C. for 2 hours. The wet catalyst was dried overnight at 102° C. A second impregnation was performed on the dried material using 120 ml of an aqueous solution of cobalt nitrate containing 87.15 g cobalt nitrate. The wet catalyst was dried again at 124° C. overnight. The final catalyst contained 35 wt. % cobalt on a water free basis. The catalyst was screened to a 38-106 micron fraction. The Fischer-Tropsch conversion results are contained in Table 1.

EXAMPLE 4

138.73 g of cobalt nitrate was added to a 20% aqueous solution of zirconium nitrate, $Zr(NO_3)_4.5H_2O$, in an amount of 82.74 g, and the final volume made up to 132 ml. This solution was added to 100 g of LaRoche Versal-900 alumina which had been first calcined at 500° C. for 2 hours. An additional 12 ml of water was added to the catalyst. After about an hour, the catalyst was transferred to an oven and dried at 103° C. for about 8 hours. The final catalyst, which contained 2.5 wt. % zirconium and 20.0 wt. % cobalt on a water free basis, was screened to a 38-106 micron fraction. This sample was designated Example 4a.

A portion of the catalyst of Example 4a was calcined in air by heating to 300° C. over a period of 2 hours, holding at this temperature for 1 hr and then heating to about 495° C. over a period of 1 hour, at which point the power to the calciner was turned off and the catalyst allowed to cool overnight. This sample was designated 4b. The Fisher-Tropsch conversion results for both Examples 4a and 4b are contained in Table 1.

EXAMPLE 5

Ammonium molybdate, 8.12 g, was dissolved in 60° C. water and made up to 150 ml. The molybdenum solution was then added to 125 g of Versal 900 previously calcined at 500° C. for 2 hours. The wet molybdenum-alumina was dried at 100° C. for 4 hours and then impregnated with a solution of 174.3 g of cobalt nitrate made up to 145 ml. The catalyst was dried at 100° C. overnight. The final catalyst contained 2.5 wt. % molybdenum and 20 wt. % cobalt on a water free basis. The Fischer-Tropsch conversion results are contained in Table 1.

Catalysts prepared in Examples 2, 3, 4 (part 1) and 5 were hydrogen calcined and reduced at 350° C.

EXAMPLE 6

A commercially available hydrodesulfurization cobalt-molybdenum catalyst, Crosfield 465, was ground and screened to a particle size range of 15 to 106 microns. The manufacturer quotes the typical cobalt and molybdenum contents as 3.8 weight % and 12.3 weight % respectively. This catalyst was tested in the same way as the catalysts of the other examples. The results of testing are shown in Table 1.

DISCUSSION OF TEST RESULTS

Table 1 summarizes the results of Examples 1 through 6.

The catalysts of Examples 1 through 3 illustrate the effectiveness of catalysts with about 16% to 35% cobalt supported on various alumina supports.

When compared to the catalysts of Examples 1 and 2, the catalyst of Example 5 shows an unexpected improvement in activity when 2.5 wt. % molybdenum is included in the composition. Reference to Table 1 demonstrates an unexpected improvement in activity, as expressed by the relative rate of reaction of carbon monoxide (as defined above in the "Treatment of Results" section). The activity of the catalyst of Example 5 is between 56% and 70% higher than that of the prior art type catalysts of Examples 1 and 2, which contain only cobalt at about the same level as that of Example 5. The catalyst of Example 3, containing 35% cobalt, has a similar relative rate of carbon monoxide conversion at 24 hours. This is a further demonstration of the surprising promotional effect of a small amount of molybdenum. This is all the more surprising in view of the lack of activity of the commercial cobalt-molybdenum catalyst of Example 6.

When 2.5 wt. % zirconium is incorporated with cobalt, as represented by Examples 4a and 4b, an unexpected improvement in activity occurs, as expressed by the relative rate constant (as defined in the "Treatment of Results" section) which is based on the conversion of carbon monoxide. Thus, when the catalysts of Examples 4a and 4b are compared with those of Examples 1 and 2, which contain a similar amount of cobalt but no zirconium, it is seen that the relative activity of the catalysts of this invention are higher by a factor of about 2 than catalysts without zirconium.

The catalysts of Example 4a and 4b differ Catalyst 4a was dried at 108 C. and subsequently reduced in hydrogen at a higher temperature, whereas Catalyst 4b was calcined in air at 495 C. before reduction at 350 C. Further, reference to Table 1 indicates that the catalysts of Example 4 show an unexpected improvement in product selectivities when zirconium is included in the composition. Specifically, the selectivity for the formation of desirable liquid hydrocarbons, as expressed by the C5+ selectivity, is unexpectedly improved, while at the same time the amount of less desirable oxygen containing products such as methanol and ethanol is unexpectedly decreased. Examination of Table 1 demonstrates a further unexpected result.

A mixed promoter catalyst having the same cobalt content and with 1.25% molybdenum and 1.25% zirconium would be more active than one with molybdenum alone and almost as active as with zirconium. It would be nearly twice as active as unpromoted cobalt catalyst.

The Schulz-Flory alpha values are determined from a carbon-number distribution obtained by analysis of reactor products taken at the longest operating times. The Schulz-Flory alpha value is defined as the probability of chain growth step to the next higher carbon number divided by the sum of the growth step probability plus the chain termination probability. This parameter can be used to estimate the distribution of carbon number products and thereby the effectiveness of the process to make liquid products with a particular carbon distribution.

Alpha values in experimental systems depend on the nature of the catalyst and on the fundamental operating conditions to which the catalyst is exposed. As a consequence, evaluation of differences between different catalysts must be done at a common set of operating conditions. Catalysts were accordingly compared at a common set of conditions herein. Table 3 (Summary of Alpha Values) depicts the data collected from six separate tests, as described in Table 1. The alpha values refer to two kinds of measurements for each catalyst test. The alpha determined from the higher carbon number products is the value determined from the analysis of the reactor wax, which is that hydrocarbon remaining in the reactor at the end of the test period.

The average alpha value for the two tests employing the catalysts of Example 4 is 0.88, which is significantly higher than the average alpha value of 0.84 obtained with the catalysts of Examples 1 and 2, which are catalysts with similar levels of cobalt but no zirconium. Thus, the alpha values, which are a direct indication of the yield of liquid products having boiling points in the range of the most desirable products, namely gasoline and diesel, are unexpectedly the highest when zirconium is incorporated with cobalt.

The alpha values determined from lower carbon number products were obtained from the analysis of a proportional collection of products obtained near the end of the test period. The liquid products were blended and analyzed. These are products with carbon numbers in a range lower than that of the starting liquid, i.e., lower than 30. The data contained in Table 3 shows that, when the catalysts of Examples 1, 2 and 4 are compared, the addition of zirconium does not effect the value of alpha for products in the lower carbon number range. However, the unexpected advantage of the addition of zirconium is additionally evident in the higher $C_5+$ selectivity values as pointed out above.

This same advantageous result would result from the use of a mixed promoter—molybdenum and zirconium catalyst. Thus, a catalyst having the same cobalt content and with 1.25% molybdenum and 1.25% zirconium would be much more selective for $C_5+$ products than unpromoted cobalt catalysts or catalysts promoted with molybdenum alone. Any ratio of molybdenum to zirconium will have an advantageous effect, but ratios above 0.5 Mo to 1 Zr are especially desirable.

These representative embodiments are illustrative of the invention, but other modifications and variations are within the scope of the following claims.

TABLE 1

SUMMARY OF STIRRED AUTOCLAVE FISCHER TROPSCH RESULTS
TEMPERATURE = 230 C., HYDROGEN TO CO MOLE RATIO = 2

| EXAMPLE | 1 | 2 | 3 | 4A | 4B | 5 | 6 |
|---|---|---|---|---|---|---|---|
| CATALYST | W1 | W3 | W21 | W16 | W16C2 | W19 | W22 |
| SUPPORT (1) | CATAPAL AL | V900 AL | V900 AL | V900 AL | V900 AL | V900 AL | Commercial HDS Co/Mo CATALYST |
| CATALYST METALS | | | | | | | |
| Co % | 16.7 | 20 | 35 | 20 | 20 | 20 | 3.8 |
| Mo % | | | | | | 2.5 | 12.3 |
| Zr % | | | | 2.5 | 2.5 | | |
| PRESSURE PSIG | 250 | 250 | 200 | 175 | 200 | 175 | 250 |
| RUN No. | 130 | 134 | 144 | 141 | 143 | 142 | 145 |
| CATALYST WT GM | 44.8 | 38.6 | 40.9 | 37.6 | 30.3 | 28.6 | 3.8 |
| GAS RATE: | | | | | | | |
| NL/HR | 135 | 135 | 201.4 | 135 | 135 | 135 | 24 |
| NL/HR/GM CAT | 3.0 | 3.5 | 4.95 | 3.59 | 4.46 | 4.72 | 3.14 |
| TIME ON LINE 24 HOURS | | | | | | | |
| CO FEED NL/HR | 45 | 45 | 65 | 45 | 45 | 45 | 45 |
| CO CONVERSION: % | 68.4 | 62.0 | 65.0 | 77.2 | 66.5 | 62.6 | 3.8 |

TABLE 1-continued

SUMMARY OF STIRRED AUTOCLAVE FISCHER TROPSCH RESULTS
TEMPERATURE = 230 C., HYDROGEN TO CO MOLE RATIO = 2

| EXAMPLE | 1 | 2 | 3 | 4A | 4B | 5 | 6 |
|---|---|---|---|---|---|---|---|
| $CH_4$ Selectivity: % | 8.7 | 9.4 (3) | 8.3 | 6.6 | 7.1 | 9.7 | — |
| $CO_2$ Selectivity: % | 2.7 | 2.8 (3) | 3.0 | 5.6 | 2.8 | 3.7 | — |
| KO | 1.2 | 0.96 | 1.53 | 1.7 | 1.2 | 0.98 | — |
| KO* (CORRECTED) (5) | 1.06 | 0.84 | 1.53 | 1.83 | 1.2 | 1.05 | — |
| K | 1.06 | 0.98 | 1.68 | 2.04 | 1.78 | 1.65 | — |
| RELATIVE ACTIVITY | 1.08 | 1.00 | 1.71 | 2.08 | 1.82 | 1.68 | — |
| C5+ Selectivity: % @ 24 HR. | 79.1 (2) | 80.0 (3) | 83.3 | 86.1 | 84.6 | 81.0 | — |
| ALPHA (4) | 0.832 | 0.847 | 0.864 | 0.851 | 0.916 | 0.806 | — |
| @ HOUR | 216 | 168 | 288 | 120 | 96 | 120 | — |

(1) AL = ALUMINA, ZEO = ZEOLITE, V = VERSAL
(2) DATA AFTER 72 HOURS AND 60% CO CONVERSION
(3) DATA AFTER 48 HOURS AND 62% CO CONVERSION
(4) BASED ON REACTOR WAX ANALYSIS
(5) CORRECTED TO 215 PSIA BY RATIO OF PRESSURES TO THE POWER 0.6

TABLE 2

PHYSICAL PROPERTIES OF CATALYST SUPPORTS

| SUPPORT | VERSAL 900 | VERSAL GH | VISTA CATAPAL |
|---|---|---|---|
| CATALYST EXAMPLE | 3, 5, 4A, 4B, | 2 | 1 |
| CATALYST No. | 21, 19, 16, 16C2 | 3 | 1 |
| SUPPORT ANALYSES | | | |
| Calcination Temp C. | 500 | 850 | 500 |
| Calination time: hr | 2 | 1 | 6 |
| Surface Area: m2/g | 221 | 223 | 236 |
| Mercury Pore Vol.: ml/g | .483 | 0.600 | 0.376 |

What is claimed is:

1. A slurry reactor process useful for the conversion, at reaction conditions, of synthesis gas to hydrocarbons wherein the selectivity to $C_5$ plus hydrocarbons is above 80% in a slurry reaction process which comprises reacting a mixture of hydrogen and carbon monoxide in molar ratio of about 2.5:1 to 1.5:1 at a temperature in the range of about 190° to 300° C.; a reactor pressure in the range of about 50 to 650 psig; a space velocity of about 100 to 15000 volumes of gaseous feed (at standard temperature and pressure) per volume of dry catalyst in the slurry per hour, with a catalyst comprised of cobalt and zirconium that has been deposited on an alumina support by impregnation from an aqueous solution of salts of the cobalt and zirconium, respectively, the catalyst containing from about 5% to 35% cobalt and from about 0.1% to 10% zirconium based on the total weight of the catalyst and the alumina support having an initial particle size in the range of from about 5 to 250 microns in the mixture and recovering the product.

TABLE 3

SUMMARY OF ALPHA VALUES
TEMPERATURE = 230 C., H2/CO MOLE RATIO = 2

| EXAMPLE | 1 | 2 | 3 | 4A | 4B | 5 |
|---|---|---|---|---|---|---|
| SUPPORT | CATAPAL | V900 | V900 | V900 | V900 | V900 |
| CATALYST METALS | | | | | | |
| CO % | 16.7 | 20 | 35 | 20 | 20 | 20 |
| Zr % | | | | 2.5 | 2.5 | |
| Mo % | | | | | | 2.5 |
| PRESSURE PSIG | 250 | 250 | 200 | 175 | 200 | 175 |
| RUN No. | 130 | 134 | 144 | 141 | 143 | 142 |
| CATALYST WT GM | 44.8 | 38.6 | 40.9 | 37.6 | 30.3 | 28.6 |
| GAS RATE: | | | | | | |
| NL/HR | 135 | 135 | 201.4 | 135 | 135 | 135 |
| NL/HR/GM CAT | 3.0 | 3.5 | 4.95 | 3.59 | 4.46 | 4.75 |
| CO FEED NL/HR | 45 | 45 | 65 | 45 | 45 | 45 |
| ALPHA (1) | 0.832 | 0.847 | 0.864 | 0.851 | 0.916 | 0.806 |
| @ HOUR | 216 | 168 | 288 | 120 | 96 | 120 |
| CARBON No. RANGE | 20–58 | 50–66 | 45–74 | 50–70 | 55–65 | 50–60 |
| ALPHA (2) | 0.82 | 0.79 | 0.844 | 0.79 | 0.824 | 0.81 |
| @ HOUR | 216 | 168 | 192 | 120 | 96 | 120 |
| CARBON No. RANGE | 9–14 | 10–15 | 9–18 | 4–15 | 9–17 | 9–15 |

(1) BASED ON ANALYSIS OF REACTOR WAX NEAR THE END OF THE RUN
(2) BASED ON ANALYSIS OF TOTAL REACTOR PRODUCTS NEAR THE END OF RUN

2. The process of claim 1, wherein the molar ratio of the hydrogen and carbon monoxide is between 2:1 and 1.6:1, the temperature is in the range of 200° to 260° C., the reactor pressure is in the range of 100 to 650 psig.

3. The process of claim 1 in which the catalyst also contains molybdenum deposited on the alumina support from an aqueous solution of molybdenum.

4. The process of claim 1 wherein the process is carried out in one or more bubble column reactors.

5. The process of claim 1, in which the catalyst comprises from 10% to 20% by weight cobalt, 1% to 10% zirconium and molybdenum and in an amount up to 9% weight based on dry catalyst, the zirconium to molybdenum being above about 2.

6. The process of claim 5 in which the CO conversion is each of the reactors is in excess of about 40% and the alpha value of the $C_5$ plus liquid products produced exceeds about 0.8.

7. The process of claim 1 wherein the catalyst, comprises from about 10% to 35% cobalt, from about 0.5% to 5% molybdenum and from about 0.5% to 5% zirconium.

8. The process of claim 1 the said inorganic oxide is gamma alumina or an alumina having the characteristics of VERSAL 900.

9. The process of claim 1, wherein the support is alumina which has a surface area of at least about 45 $m^2/g$ and a pore volume of at least about 0.3 $cm^3/g$.

10. A slurry reactor process useful for the conversion of hydrogen and carbon monoxide to hydrocarbons in a slurry reaction process which comprises reacting hydrogen and carbon monoxide at a temperature in the range of about 190° to 300° C.; a reactor pressure in the range of about 50 to 400 psig; a space velocity of about 100 to 15000 volumes of gaseous feed (at standard temperature and pressure) per volume of dry catalyst in the slurry per hour, with a catalyst comprised of molybdenum, cobalt and an inorganic oxide support, the catalyst containing from about 2% to 50% cobalt and from about 0.1% to 15% molybdenum based on the total weight of the catalyst and the weight ratio of molybdenum to cobalt being from about 0.02 to 0.25 and the alumina support having a particle size of about 5 to 250 microns and recovering the product.

* * * * *